United States Patent
Sheng et al.

(10) Patent No.: US 11,208,382 B2
(45) Date of Patent: Dec. 28, 2021

(54) ENTINOSTAT-CONTAINING COMPOUND, CRYSTAL FORM OF COMPOUND THEREOF, AND PREPARATION METHOD THEREFOR AND PHARMACEUTICAL COMPOSITION THEREOF

(71) Applicant: Hangzhou SoliPharma Co., Ltd., Zhejiang (CN)

(72) Inventors: Xiaohong Sheng, Zhejiang (CN); Xiaoxia Sheng, Zhejiang (CN)

(73) Assignee: Hangzhou Solipharma Co., Ltd., Zhejiang (CN)

( * ) Notice: Subject to any disclaimer, the term of this patent is extended or adjusted under 35 U.S.C. 154(b) by 25 days.

(21) Appl. No.: 16/634,797

(22) PCT Filed: Jul. 28, 2017

(86) PCT No.: PCT/CN2017/094851
§ 371 (c)(1),
(2) Date: Apr. 17, 2020

(87) PCT Pub. No.: WO2019/019130
PCT Pub. Date: Jan. 31, 2019

(65) Prior Publication Data
US 2020/0270213 A1    Aug. 27, 2020

(51) Int. Cl.
*C07D 213/30* (2006.01)
*C07C 57/15* (2006.01)

(52) U.S. Cl.
CPC ............ *C07D 213/30* (2013.01); *C07C 57/15* (2013.01); *C07B 2200/13* (2013.01)

(58) Field of Classification Search
CPC .................................................. C07D 213/30
USPC ..................................................... 514/357
See application file for complete search history.

(56) References Cited

U.S. PATENT DOCUMENTS 6,174,905 B1 * 1/2001 Suzuki ................. C07D 413/12
                                                                514/346
7,973,166 B2    7/2011 Schneider et al.

FOREIGN PATENT DOCUMENTS

| CN | 102137846 A1 | 7/2011 | |
|----|-------------|--------|---|
| JP | 10152462 | * 9/1998 | .......... C07C 237/42 |
| JP | 4360660 B2 | 11/2009 | |
| WO | WO 2004058234 | * 7/2004 | ............ A61K 31/00 |
| WO | WO-2019019130 A1 | 1/2019 | |

OTHER PUBLICATIONS

International Search Report and Written Opinion in International Application No. PCT/CN2017/094851, State Intellectual Property Office of the P.R. China, China, dated May 8, 2018, 14 pages.

* cited by examiner

Primary Examiner — Nizal S Chandrakumar
(74) Attorney, Agent, or Firm — Sterne, Kessler, Goldstein & Fox P.L.L.C.

(57) ABSTRACT

The present invention relates to a compound formed by entinostat as shown in formula (I) and acidic counterion. Compared with the known solid form of entinostat, the compound involved has advantages in terms of solubility, stability, etc. The present invention also relates to a crystalline form of the compound and a preparation method therefor, a pharmaceutical composition thereof and the use thereof in the preparation of a drug for preventing and/or treating a disease associated with differentiation or proliferation.

(I)

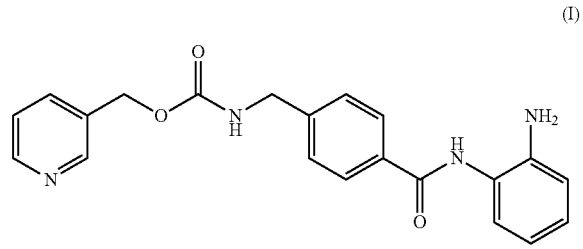

12 Claims, 7 Drawing Sheets

ENTINOSTAT-CONTAINING COMPOUND, CRYSTAL FORM OF COMPOUND THEREOF, AND PREPARATION METHOD THEREFOR AND PHARMACEUTICAL COMPOSITION THEREOF

FIELD OF THE INVENTION

The present invention relates to compounds formed by entinostat and acids, specifically, relates to crystalline forms, preparation methods, pharmaceutical compositions and uses thereof.

BACKGROUND

Entinostat, also named as MS-275, with the chemical name of N-(2-aminophenyl)-4-[N-(pyridin-3-yl)methoxycarbonyllaminomethyl]benzamide, is a histone deacetylase inhibitor. The chemical structure is shown in the following formula (I):

Patent document U.S. Pat. No. 6,174,905B1 reported the synthesis method of the compound entinostat and provided the data of melting point and infrared spectrum. Patent document CN102137846 B disclosed polymorph A, polymorph B, polymorph C of entinostat and amorphous entinostat, and provided XRD, DSC, FT-Raman and FT-IR patterns. The present inventors found that the polymorphs A, B and C of entinostat obtained according to the preparation methods of Example 48 in U.S. Pat. No. 6,174,905B1 and Example 1 in CN102137846 B have the defects of low solubility in water. Entinostat in the result of Comparative Example 4 in patent JP4360660B2 had an apparent chemical impurity and could not be purified by recrystallization from solvents. In addition, as known to those skilled in the art, most amorphous materials have the defects of unstable phase, susceptible hygroscopicity and poor flowability.

In view of the defects in the prior art, there is a need to develop new crystalline forms of entinostat with more improved properties to meet the strict requirements for pharmaceutical formulations on several chemico-physical properties including solubility, stability, and morphology of active substances.

SUMMARY OF THE INVENTION

In view of the defects in the prior art, the purpose of the present invention is to provide compounds formed by entinostat and acid counterion, their crystalline forms and preparation methods, pharmaceutical compositions and uses thereof. The compounds are stable crystalline solids and have one or more improved properties, especially in terms of crystallinity, solubility, hygroscopicity, morphology, processability of the formulation, crystal stability, chemical stability, and the like.

According to the purpose of the present invention, one aspect of the present invention is to provide the compound (hereinafter referred to as Compound A) formed by entinostat and fumaric acid, its crystalline form (hereinafter referred to as Crystalline Form of Compound A or Crystalline Compound A) and their preparation methods.

Compound A, with a structural formula shown in the following formula (II), is formed by entinostat and fumaric acid, wherein the molar ratio of entinostat to fumaric acid is 1:0.5.

Compound A is a co-crystal or a salt formed by entinostat and fumaric acid, preferably a co-crystal.

In a preferred embodiment of the present invention, Compound A is crystalline, preferably, a non-solvate, a hydrate, or an anhydrous form, and more preferably an anhydrous form.

Figure 4:
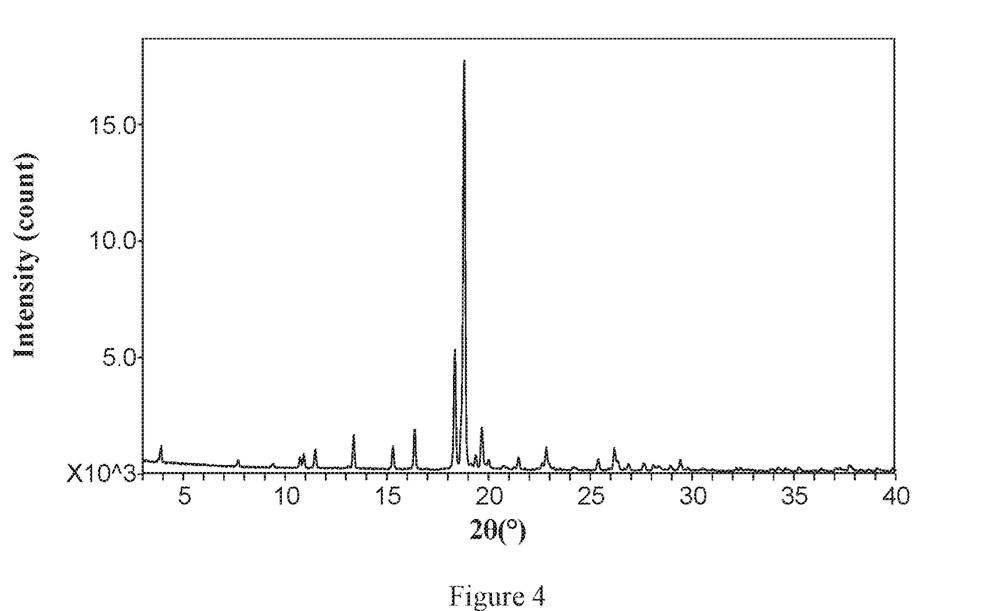
FIG. 4 is the XRPD pattern of Crystalline Form of Compound A of the present invention.

In a more preferred embodiment, measured using Cu-Kα radiation, the X-ray powder diffraction pattern of the Crystalline Form of Compound A, has the following characteristic peaks at 2θ values of 3.9°±0.2°, 13.4°±0.2°, 16.4°±0.2° and 18.8°±0.2°; and has the following characteristic peaks at 2θ values of 11.5°±0.2°, 15.3°±0.2°, 18.3°±0.2° and 19.7°±0.20; and has the following characteristic peaks at 2θ values of 7.7°±0.2°, 10.9°±0.2°, 22.8°±0.2° and 26.2°±0.2°. Non-restrictively, in one specific embodiment of the present invention, the XRPD pattern of Crystalline Form of Compound A is shown in FIG. 4.

In a preferred embodiment of the present invention, the Fourier transform infrared spectrum of Compound A has characteristic peaks at wave numbers of $3369\ cm^{-1}\pm 2\ cm^{-1}$, $1713\ cm^{-1}\pm 2\ cm^{-1}$, $1664\ cm^{-1}\pm 2\ cm^{-1}$, $1605\ cm^{-1}\pm 2\ cm^{-1}$, $1556\ cm^{-1}\pm 2\ cm^{-1}$, $1504\ cm^{-1}\pm 2\ cm^{-1}$, $1282\ cm^{-1}\pm 2\ cm^{-1}$, $1248\ cm^{-1}\pm 2\ cm^{-1}$, $1220\ cm^{-1}\pm 2\ cm^{-1}$, $1135\ cm^{-1}\pm 2\ cm^{-1}$, $1044\ cm^{-1}\pm 2\ cm^{-1}$, $759\ cm^{-1}\pm 2\ cm^{-1}$, $712\ cm^{-1}\pm 2\ cm^{-1}$ and $640\ cm^{-1}\pm 2\ cm^{-1}$.

Compared with entinostat in the prior art, Compound A of the present invention has the following beneficial properties:
  (1) According to Comparative Example 1, Compound A of the present invention has better solubility in water.
  (2) According to the XRPD pattern, Compound A of the present invention has better crystallinity.
  (3) According to Comparative Example 2, Compound A of the present invention has excellent phase stability.
  (4) According to Comparative Example 3 of the present invention, Compound A of the present invention has lower impurity level (at RRT=1.403), less impurities, higher chemical purity, and has excellent chemical stability under the condition of room temperature, high temperature, high humidity and accelerated conditions.

The above beneficial properties indicate that: compared to entinostat in the prior art, Compound A of the present invention has more beneficial properties. Entinostat in the prior art has low solubility, while Compound A of the present invention has high solubility in water and has higher dissolution and bioavailability. In addition, Compound A has good phase stability, which can better ensure the quality, safety and stability of the active ingredient itself and the formulations containing entinostat during manufacture and storage, and avoid problems such as poor content uniformity of active ingredients, increased impurities, and also special and expensive packaging.

The present invention provides a preparation method of Compound A, which comprises direct reaction of entinostat with 0.5 equivalent to 1 equivalent of fumaric acid, preferably an acid-base reaction in an organic solvent or a mixed solvent. The organic solvent is a solvent capable of dissolving entinostat or fumaric acid.

The present invention provides a method of preparing Crystalline Form of Compound A, including any one of the following methods:

(1) Dissolving entinostat and fumaric acid respectively in a solvent to form solutions, then mixing the solutions and stirring for crystallization, and then separating the precipitated crystals, and drying to obtain Crystalline Form of Compound A.
  Preferably, entinostat and fumaric acid use the same solvent to form solutions;
  Preferably, the solvent is selected from the group consisting of an alcohol and a ketone, more preferably ethanol;
  Preferably, the mass-volume ratio of entinostat to solvent when the solution is formed is from 10 mg/mL to 100 mg/mL, more preferably from 10 mg/mL to 30 mg/mL;
  Preferably, the molar ratio of entinostat to fumaric acid ranges from 1:0.5 to 1:1.0; more preferably from 1:0.6 to 1:0.7;
  Preferably, the duration for stirring is from 1 to 3 days;
  Preferably, the operation is performed at 10° C. to 40° C., more preferably at room temperature.

(2) Forming a solution with the mixture of entinostat and fumaric acid in a solvent, and then drying the solvent by volatilization to obtain Crystalline Form of Compound A;
  Preferably, the solvent is selected from the group consisting of an alcohol and a ketone, more preferably ethanol;
  Preferably, the mass-volume ratio of entinostat to solvent when the solution is formed ranges from 5 mg/mL to 50 mg/mL, more preferably from 5 mg/mL to 20 mg/mL;
  Preferably, the molar ratio of entinostat to fumaric acid ranges from 1:0.5 to 1:1.0; more preferably from 1:0.6 to 1:0.7;
  Preferably, the volatilization process is performed at 10° C. to 40° C., more preferably at room temperature.

According to the purpose of the present invention, another aspect of the present invention is to provide the compound (hereinafter referred to as Compound B) formed by entinostat and maleic acid, its crystalline form (hereinafter referred to as Crystalline Form of Compound B or Crystalline Compound B) and their preparation methods.

Compound B, with a structural formula shown in the following formula (III), is formed by entinostat and maleic acid, wherein the molar ratio of entinostat to maleic acid is (III)

Compound B is a co-crystal or a salt formed by entinostat and maleic acid, preferably a co-crystal.

Figure 5:
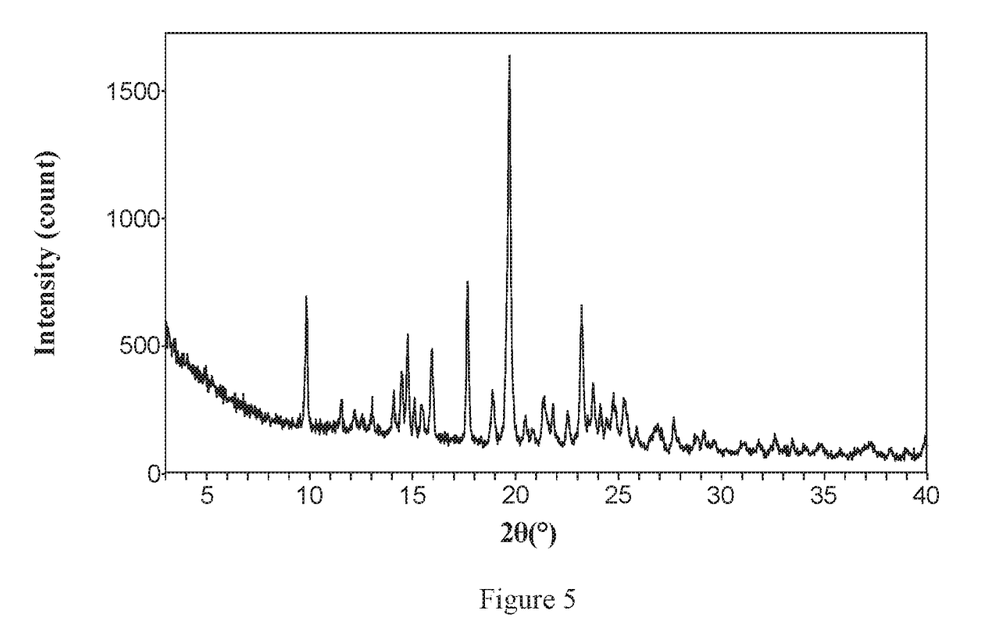
FIG. 5 is the XRPD pattern of Crystalline Form of Compound B of the present invention.

In a preferred embodiment of the present invention, Compound B is crystalline, preferably, a non-solvate, a hydrate, or an anhydrous form, and more preferably an anhydrous form. In a more preferred embodiment, measured using Cu-Kα radiation, the X-ray powder diffraction pattern of the Crystalline Form of Compound B, has the following characteristic peaks at 2θ values of 9.8°±0.2°, 15.9°±0.2°, 19.7°±0.2° and 23.2°±0.2°; and has the following characteristic peaks at 2θ values of 14.1°±0.2°, 14.8°±0.2°, 17.7°±0.2° and 18.9°±0.2; and has the following characteristic peaks at 2θ values of 14.5°±0.2°, 21.4°±0.2°, 23.8°±0.2° and 24.8°±0.2°. Non-restrictively, in one specific embodiment of the present invention, the XRPD pattern of the Crystalline Form of Compound B is shown in FIG. 5.

In a preferred embodiment of the present invention, the Fourier transform infrared spectrum of Compound B has characteristic peaks at wave numbers of 3298 $cm^{-1}$±2 $cm^{-1}$, 1718 $cm^{-1}$2 $cm^{-1}$, 1545 $cm^{-1}$±2 $cm^{-1}$, 1499 $cm^{-1}$±2 $cm^{-1}$, 1363 $cm^{-1}$2 $cm^{-1}$, 1313 $cm^{-1}$2 $cm^{-1}$, 1248 $cm^{-1}$±2 $cm^{-1}$, 1147 $cm^{-1}$±2 $cm^{-1}$, 1044 $cm^{-1}$±2 $cm^{-1}$, 992 $cm^{-1}$±2 $cm^{-1}$, 860 $cm^{-1}$±2 $cm^{-1}$, 750 $cm^{-1}$±2 $cm^{-1}$, 703 $cm^{-1}$±2 $cm^{-1}$ and 645 $cm^{-1}$±2 $cm^{-1}$.

Compared with entinostat in the prior art, Compound B of the present invention has the following beneficial properties:
  (1) According to Comparative Example 1, Compound B of the present invention has better solubility in water.
  (2) According to Comparative Example 2, Compound B of the present invention has excellent phase stability.
  (3) According to Comparative Example 4, Compound B of the present invention can be more easily purified through recrystallization from solvents.

The above beneficial properties indicate that: compared to entinostat in the prior art, Compound B of the present invention has more beneficial properties. Entinostat in the prior art has low solubility, while Compound B of the present invention has high solubility in water, and has higher dissolution and bioavailability. In addition, Compound B has good phase stability, which can better ensure the quality, safety and stability of the active ingredient itself and the formulations containing entinostat during manufacture and storage, Compound B of the present invention can be more easily purified, and the process production cost is lower.

The present invention provides a method of preparing Compound B, which comprises direct reaction of entinostat with 1 equivalent to 1.5 equivalent of maleic acid, preferably an acid-base reaction in an organic solvent or a mixed solvent. The organic solvent is a solvent capable of dissolving entinostat or maleic acid.

The present invention provides a method of preparing Crystalline Form of Compound B, including any one of the following methods:

(1) Dissolving entinostat and maleic acid respectively in a solvent to form solutions, then mixing the solutions and stirring it for crystallization, and then separating the precipitated crystals, and drying to obtain Crystalline Form of Compound B;

Preferably, entinostat and maleic acid use the same solvent to form solutions;

Preferably, the solvent is selected from the group consisting of alcohols and ketones, more preferably ethanol;

Preferably, the mass-volume ratio of entinostat to solvent when the solution is formed ranges from 10 mg/mL to 100 mg/mL, more preferably from 10 mg/mL to 30 mg/mL;

Preferably, the molar ratio of entinostat to maleic acid ranges from 1:1.0 to 1:1.5; more preferably from 1:1.0 to 1:1.2;

Preferably, the duration for stirring is from 1 to 3 days;

Preferably, the operation is performed at room temperature;

(2) Forming a solution of the mixture of entinostat and maleic acid in a solvent, and then drying the solvent by volatilization to obtain Crystalline Form of Compound B;

Preferably, the solvent is selected from the group consisting of alcohols and ketones, more preferably ethanol;

Preferably, the mass-volume ratio of entinostat to solvent ranges from 5 mg/mL to 50 mg/mL, more preferably from 5 mg/mL to 20 mg/mL;

Preferably, the molar ratio of entinostat to fumaric acid ranges from 1:1.0 to 1:1.5; more preferably from 1:1.0 to 1:1.2;

Preferably, the volatilization process is performed at room temperature.

According to the purpose of the present invention, the third aspect of the present invention is to provide the compound (hereinafter referred to as Compound C) formed by entinostat and succinic acid, its crystalline form (hereinafter referred to as Crystalline Form of Compound C or Crystalline Compound C) and their preparation methods.

Compound C, with a structural formula shown in the following formula (IV), is formed by entinostat and succinic acid, wherein the molar ratio of entinostat to succinic acid is 1:0.5.

(IV)

Compound C is a co-crystal or a salt formed by entinostat and succinic acid, preferably a co-crystal.

Figure 6:
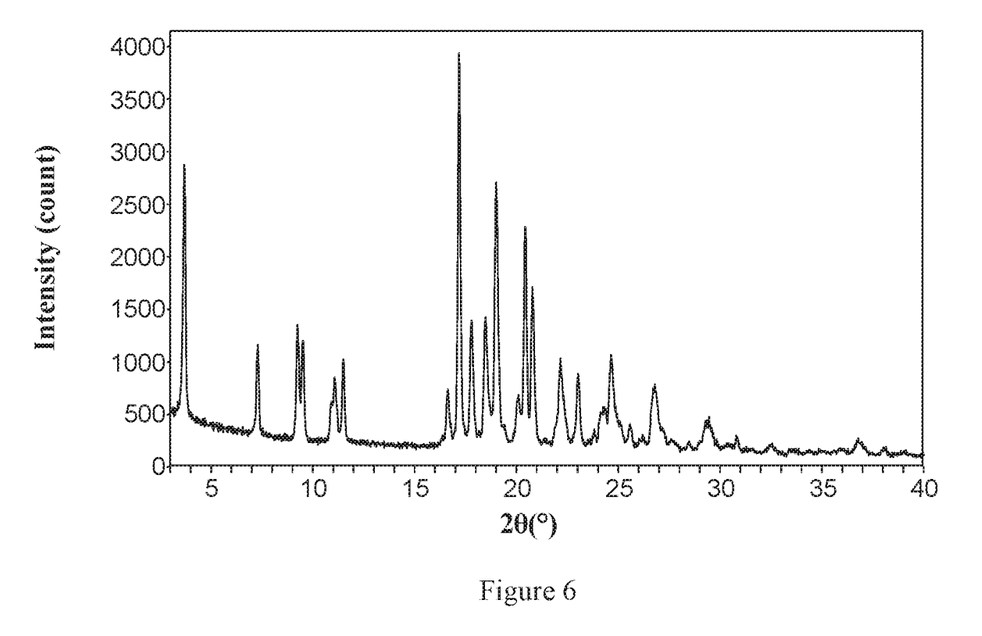
FIG. 6 is the XRPD pattern of Crystalline Form of Compound C of the present invention.

In a preferred embodiment of the present invention, measured using Cu-Kα radiation, the X-ray powder diffraction pattern of Crystalline Form of Compound C, has the following characteristic peaks at 2θ values of 3.7°±0.2°, 7.3°±0.2°, 9.2°±0.2°, 9.5°±0.2°, 16.6°±0.2°, 17.2°±0.2°, 17.8°±0.2°, 18.5°±0.2°, 19.0°±0.2°, 20.4°±0.2°, 20.8°±0.2° and 24.6°±0.2°. Non-restrictively, in one specific embodiment of the present invention, the XRPD pattern of Crystalline Form of Compound C is shown in FIG. 6.

The present invention provides a method of preparing Crystalline Form of Compound C, which comprises the following steps: forming a solution of the mixture of entinostat and succinic acid in a solvent, and then drying the solvent by volatilization to obtain Crystalline Form of Compound C.

Preferably, the mass-volume ratio of entinostat to solvent ranges from 8 to 25 mg/mL;

Preferably, the solvent is tetrahydrofuran;

Preferably, the molar ratio of entinostat to succinic acid is from 1:0.5;

Preferably, the volatilization process is performed at room temperature.

According to the purpose of the present invention, the fourth aspect of the present invention is to provide the compound (hereinafter referred to as Compound D) formed by entinostat and adipic acid, its crystalline form (hereinafter referred to as Crystalline Form of Compound D or Crystalline Compound D) and their preparation methods.

Compound D, with a structural formula shown in the following formula (V), is formed by entinostat and adipic acid, wherein the molar ratio of entinostat to adipic acid is 1:1.

(V)

Compound D is a co-crystal or a salt formed by entinostat and adipic acid, preferably a co-crystal.

In a preferred embodiment of the present invention, measured using Cu-Kα radiation, the X-ray powder diffraction pattern of Crystalline Form of Compound D has the following characteristic peaks at 2θ values of 4.0°±0.2°, 7.8°±0.2°, 11.7°±0.2°, 16.1°±0.2°, 18.7°±0.2°, 19.5°±0.2°, 20.6°±0.2°, 21.6°±0.2°, 23.7°±0.2°, 24.5°±0.2°, 25.9°±0.2° and 27.5°±0.2°.

Figure 7:
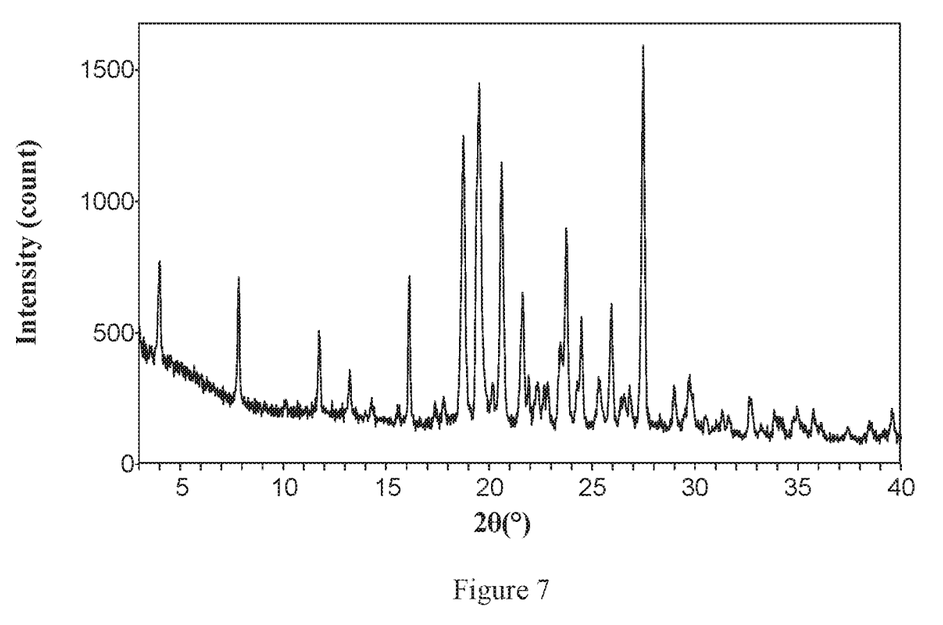
FIG. 7 is the XRPD pattern of Crystalline Form of Compound D of the present invention.

Non-restrictively, in one specific embodiment of the present invention, the XRPD pattern of Crystalline Form of Compound D is shown in FIG. 7.

The present invention provides a method of preparing Crystalline Form of Compound D, which comprises the following steps: dissolving entinostat and adipic acid respectively in a solvent to form solutions, and then mixing the solutions and stirring for crystallization, and then separating the precipitated crystals, and drying to obtain Crystalline Form of Compound D.

Preferably, entinostat and adipic acid use the same solvent to form solutions;

Preferably, the solvent is acetone;

Preferably, the mass-volume ratio of entinostat to solvent ranges from 16 mg/mL to 50 mg/mL;

Preferably, the molar ratio of entinostat to adipic acid is 1:1.25;

Preferably, the duration for stirring is from 1 to 2 days;

Preferably, the operation is performed at room temperature.

According to the purpose of the present invention, similarly, based on the methods of synthesizing Compound A, Compound B, Compound C and Compound D, similarly, salts or co-crystals can be formed by entinostat and benzenesulfonic acid, citric acid, D-gluconic acid, glycolic acid, L-lactic acid, L-malic acid, malonic acid, phosphoric acid, propionic acid, sulfuric acid, tartaric acid, p-toluenesulfonic acid, valeric acid, palmitic acid, pamoic acid, sebacic acid, stearic acid, lauric acid, acetic acid, p-chlorobenzenesulfonic acid, ethanesulfonic acid, 2-ethyl-succinic acid, fumaric acid, mucic acid, D-glucuronic acid, α-ketoglutarate, hippuric acid, hydrochloric acid, maleic acid, 1,5-naphthalene-disulfonic acid, ethanesulfonic acid, methanesulfonic acid or oxalic acid.

In each method of preparing the crystalline forms of the entinostat-containing compounds in the present invention, the raw material "entinostat" may be a known entinostat compound, a crystalline form, or an amorphous form thereof, for example, including but not limited to, entinostat obtained by referring to the preparation method in patent document U.S. Pat. No. 6,174,905B1. These patent documents are incorporated herein by reference in their entirety.

The terms used in the present invention:

"Room temperature" refers to a temperature between 10 to 30° C.

"Stirring" can be accomplished with the routine methods in the field, such as magnetic stirring, mechanical stirring, and the stirring speed ranges from 50 to 1800 r/min, preferably 300 to 900 r/min.

"Separating" can be accomplished with the routine methods in the field, such as centrifugation or filtration. Preferred method is filtration under reduced pressure, generally at a pressure less than the atmospheric pressure at room temperature, preferably less than 0.09 MPa.

"Drying" can be accomplished with the routine methods in the field, for example, drying at normal temperature, air drying, or drying under reduced pressure. Drying instruments and method are not limited, and can be a fume hood, a blast oven, a spray dryer, a fluidized bed dryer, or a vacuum oven. The pressure can be reduced pressure or atmospheric pressure, preferably less than 0.09 MPa, The drying temperature ranges from 10 to 40° C., and the duration for drying ranges from 10 to 72 hours, preferably 2 to 24 hours, and more preferably 2 to 8 hours.

The "crystalline form" in the present invention means that the compound is confirmed by the X-ray powder diffraction pattern characterization shown and has a unique and ordered molecular arrangement or configuration within the crystal lattice. It is well known to those skilled in the art that the experimental error depends on the instrument conditions, sample preparation and sample purity. The 2θ angle of the peaks in the XRD pattern usually varies slightly due to the differences in instruments and samples. The differences in peak angles can differ by 1°, 0.8°, 0.5°, 0.3°, 0.1°, etc., depending on different instruments and samples, and usually ±0.2° in differences are allowed. The relative intensity of peaks may vary with samples, sample preparation, and other experimental conditions, so the order of peak intensities cannot be the sole or determining factor. The influence of experimental factors such as sample height will cause an overall shift of the peak angles, which usually allows a certain shift. Therefore, those skilled in the art can understand that any crystalline form having the same or similar characteristic peaks as the X-ray powder diffraction pattern of the present invention belongs to the scope of the present invention. "Single crystal form" refers to a single crystal form as determined by X-ray powder diffraction.

The crystalline form of the entinostat-containing compounds according to the present invention is substantially pure and substantially free of any other crystalline or amorphous forms. When "substantially pure" in the present invention referring to a new crystalline form, it means that this new crystalline form comprises at least 80% (by weight) of the compound present, more preferably at least 90% (by weight), and especially at least 95% (by weight), especially at least 99% (by weight).

According to the purpose of the present invention, the fifth aspect of the present invention is to provide a pharmaceutical composition, which is used for treating or preventing a disease that is related to differentiation or proliferation in a mammal. The disease includes but not limited to tumors (especially malignant tumors), autoimmune diseases, skin diseases, atherosclerosis and parasitic diseases. The term "preventing" or "prevention" as used in the present invention refers to prevention of a disease or a symptom in an individual who may be predisposed to suffer from the disease or symptom but has not yet suffered or shown a disease or symptom of the disease. The term "treating" or "treatment" as used in the present invention refers to one or more of the following: (1) inhibiting the disease; for example, inhibiting the disease or symptom in an individual suffering from or showing the disease or symptom. (2) ameliorating the disease; for example, ameliorating, reversing, delaying the disease and/or symptom in an individual suffering from or showing the disease or symptom. The pharmaceutical composition comprises a therapeutically and/or preventively effective amount of pharmaceutical active ingredient selected from the crystalline forms of entinostat-containing compounds of the present invention, and at least one pharmaceutically acceptable excipient or carrier, wherein the crystalline forms of entinostat-containing compounds of the present invention at least comprise the crystalline form of a compound formed by entinostat and fumaric acid or the crystalline form of a compound formed by entinostat and maleic acid. Optionally, the pharmaceutical composition can further comprise one or more other pharmaceutically active ingredients, such as other anti-proliferative or anti-tumor drugs.

According to the present invention, the method for treating human patients comprises administrating Compound A, Compound B, Compound C or Compound D. The above compounds are prepared into formulation forms that can be administered nasally, sublingually, rectally, orally, intravenously, intramuscularly or subcutaneously, including tablets, capsules, film-coated tablets, films, suppositories, implants, injectable sterile aqueous or oil solutions, suspensions, emulsions, ointments, creams, gels, patches and nasal sprays. Compound A, Compound B, Compound C, or Compound D can be administered orally in single or multiple doses at a total dosage of 0.001 to 100 mg/kg of mammalian body weight per day. Another preferred dosage ranges from 0.01 to 0.5 mg/kg body weight per day, given orally in single or multiple doses. The specific dosage and time interval need to be adjusted according to the individual conditions of the subject, such as gender, age, weight, health conditions, tolerance, etc.

The compound can contain at least one compound specified herein, using the pharmaceutical composition made by medicinal carrier, excipient, adjuvant or using capsules, sachets, cachets, paper or absorbable carrier in other shell forms or using disposable container such as ampoules or enclosed. The carrier, excipient, adjuvant can be a solid, semi-solid or liquid material. The pharmaceutical compositions of the present invention can use carrier, excipient and adjuvant such as starch, sugar, syrup, sorbitol, mannitol, glycol, paraffin, kaolin clay, calcium silicate, silica, polyvinylpyrrolidone, calcium phosphate, cocoa butter, esters, oils, alginates, gums, methylcellulose, microcrystalline cellulose, lubricants, binders, disintegrants and so on.

The preferred pharmaceutical dosage forms of the present invention are tablets, capsules, film-coated tablets, films, suppositories, implants, injectable sterile aqueous or oil solutions, suspensions, emulsions, ointments, creams, gels, patches and nasal sprays.

SPECIFIC IMPLEMENTATIONS

The following examples will help to further understand the present invention, but are not intended to limit the contents of the present invention.

Instruments and Characterization Methods:

X-ray powder diffraction (XRPD): performed on Bruker D8 Advance diffractometer. The scan range 3-40° 2θ, step size 0.02020, and speed 0.2 s/step.

Differential thermal analysis (DSC) data were collected on TA Instruments Q200 DSC. The heating rate is 10° C./min under the protection of nitrogen purge.

Thermogravimetric analysis (TGA) data were collected on TA Instruments Q500 TGA, using High Resolution™, with the heating rate of 10° C./min under the protection of nitrogen purge.

$^1$H Nuclear magnetic resonance spectrum ($^1$H-NMR): data were collected on BrukerAvance II DMX 400 MHZ nuclear magnetic resonance spectrometer. The sample was dissolved using deuterated reagent.

Infrared spectral analysis (IR) data were collected on Bruker Tensor 27, using diffuse reflection (KBr) and ATR.

HPLC data were collected on Ultimate 3000 under the following conditions: column, YMC-Pack ODS-AQ (4.6*250 mm*5 μm); column temperature, 40° C.; flow rate, 1.5 mL/min; detection wavelength, 254 nm; injection volume 3 uL; operation time, 40 min; mobile phase, a mixture of acetonitrile: 10 mM monopotassium phosphate=1:2.

Unless particularly specified, all reagents used in the Examples were commercially available.

Unless particularly specified, all Examples were operated at room temperature.

Preparation Example 1

Entinostat was prepared by referencing the methods described in example 48 of patent document U.S. Pat. No. 6,174,905B1.

HPLC: a maximum single impurity of 1.42% at the RRT of 1.403.

Figure 1:
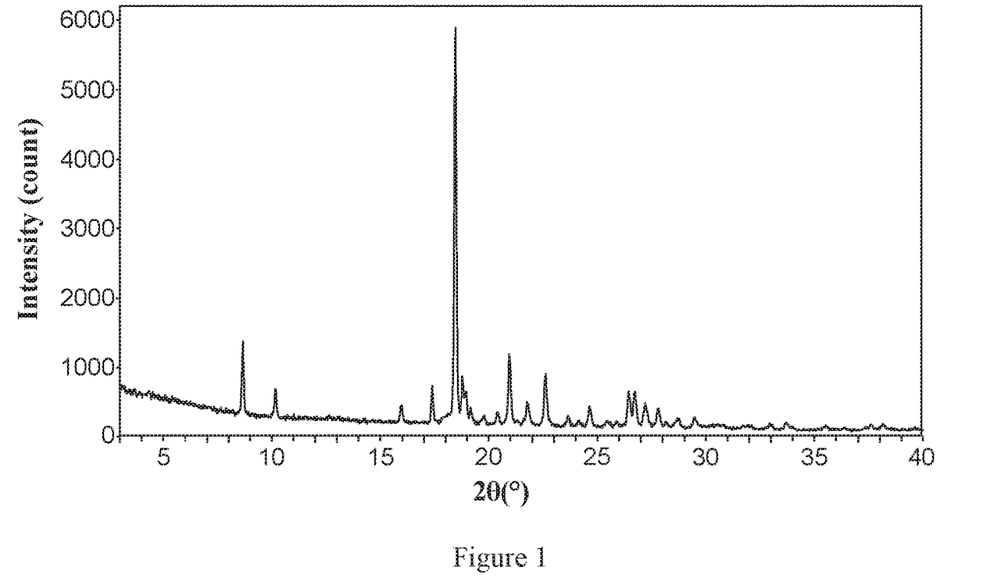
FIG. 1 is the XPRD pattern of entinostat Form A prepared with reference to U.S. Pat. No. 6,174,905B1.

The XRPD pattern is shown in FIG. 1, which is consistent with the diffraction pattern of entinostat Form A in patent document CN102137846B.

Preparation Example 2

Entinostat Form B and entinostat Form C were prepared by referencing the methods described in example 1 of patent document CN102137846B.

Figure 2:
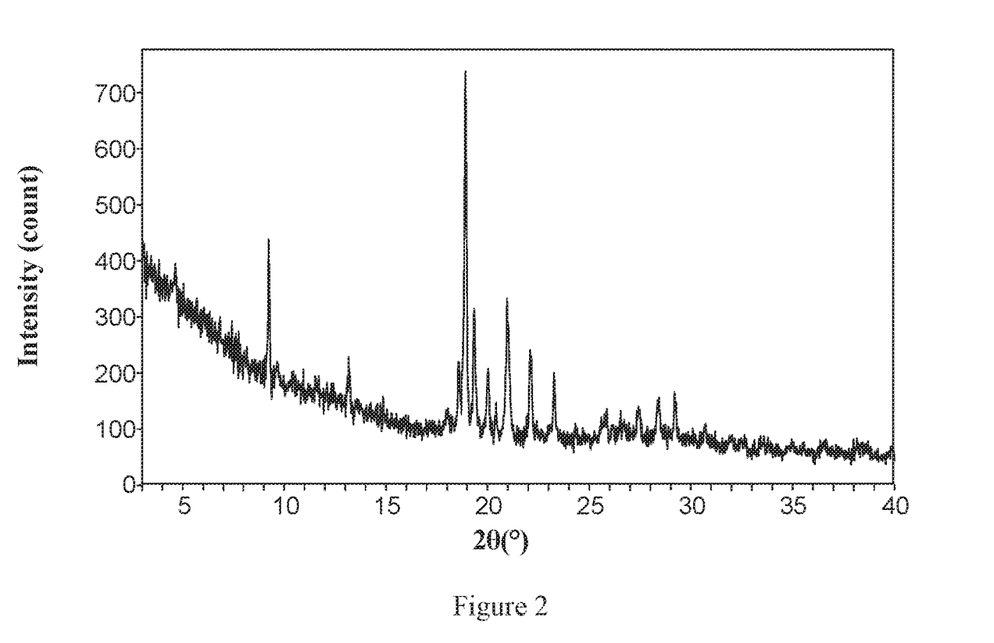
FIG. 2 is the XPRD pattern of entinostat Form B prepared with reference to CN102137846B.

The XRPD pattern of entinostat Form B is shown in FIG. 2.

HPLC: a maximum single impurity of 1.43% at the RRT of 1.403.

Figure 3:
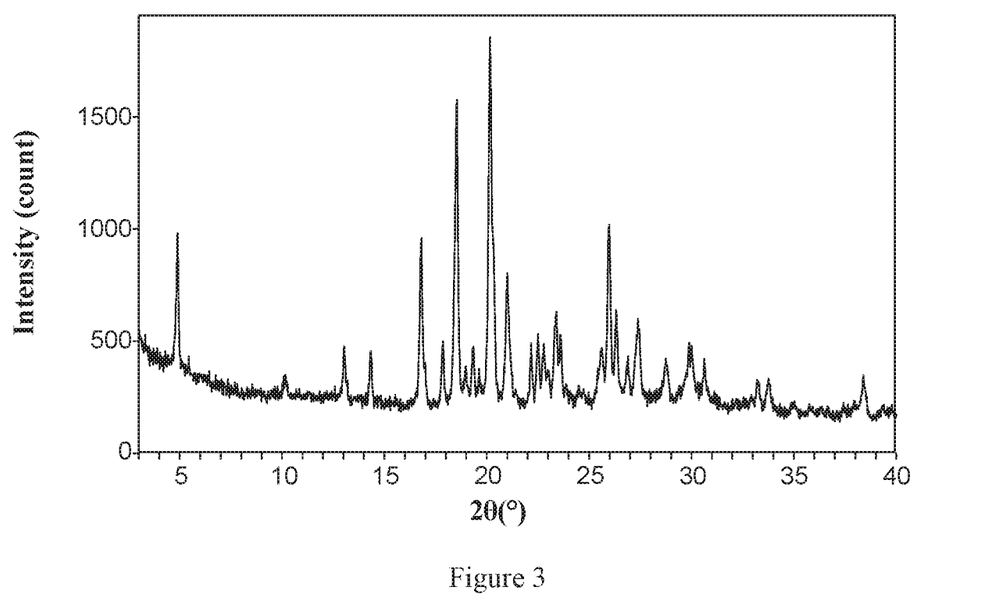
FIG. 3 is the XPRD pattern of entinostat Form C prepared with reference to CN102137846B.

The XRPD pattern of entinostat Form C is shown in FIG. 3.

There is a maximum single impurity of 1.42% at the RRT of 1.403.

Example 1

Ethanol (8 mL) was added to entinostat (80 mg) to form a solution, slowly dripping in 1 mL of fumaric acid solution (0.5 molar equivalent, in ethanol) to it. The mixture was stirred to crystallize for 2 days at room temperature, centrifuged, and dried under vacuum at room temperature to obtain Compound A (78 mg). Yield: 84%.

$^1$H-NMR (500 MHz, Methanol-d4) δ ppm: 8.58 (d, J=2.3 Hz, 1H), 8.50 (dd, J=4.9, 1.7 Hz, 1H), 7.94 (d, J=8.0 Hz, 2H), 7.89 (dt, J=7.9, 2.0 Hz, 1H), 7.50-7.35 (m, 3H), 7.22-7.16 (m, 1H), 7.09 (td, J=7.7, 1.5 Hz, 1H), 6.92 (dd, J=8.0, 1.5 Hz, 1H), 6.79 (td, J=7.6, 1.4 Hz, 1H), 6.75 (s, 1H), 5.18 (s, 2H), 4.39 (d, J=5.4 Hz, 2H), indicating that the molar ratio of entinostat to fumaric acid in Compound A is 1:0.5.

Example 2

Ethanol (2 mL) was added to entinostat (60 mg), and was heated moderately to form a solution, slowly dripping in 1 mL of fumaric acid solution (0.6 molar equivalent, in ethanol) to it. The mixture was stirred to crystallize for 3 days at room temperature, centrifuged, and dried under vacuum at room temperature to obtain Compound A (60 mg). Yield: 87%.

Its XRPD pattern is shown in FIG. 4, showing the compound is Crystalline Compound A.

Figure 8:
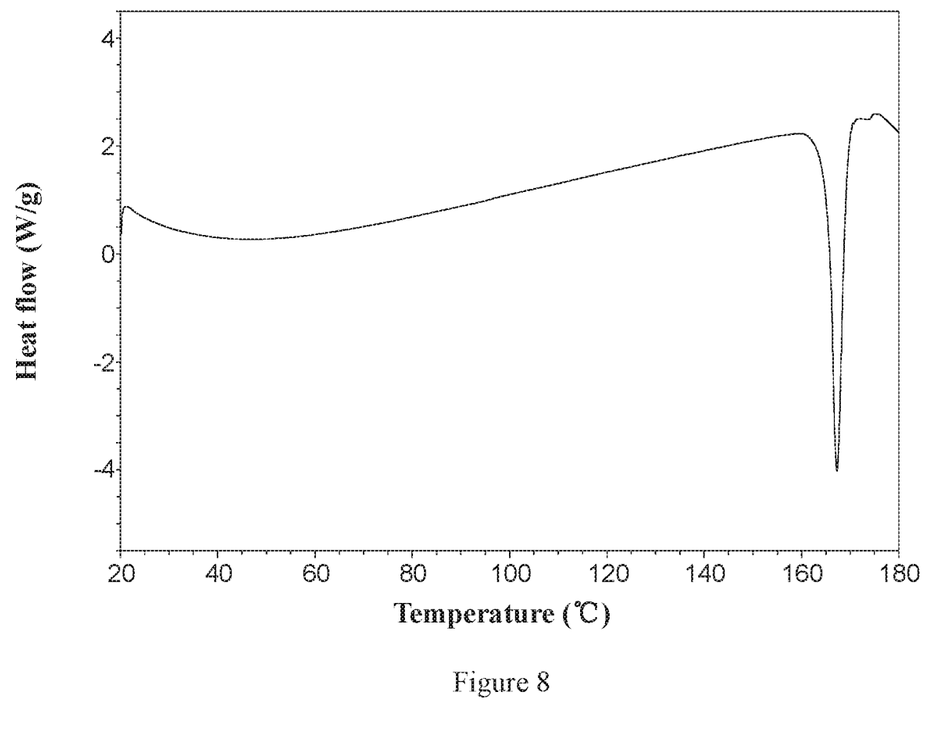
FIG. 8 is the DSC thermogram of Crystalline Form of Compound A of the present invention.

Its DSC thermogram is shown in FIG. 8, showing a melting point of 166° C.

Figure 10:
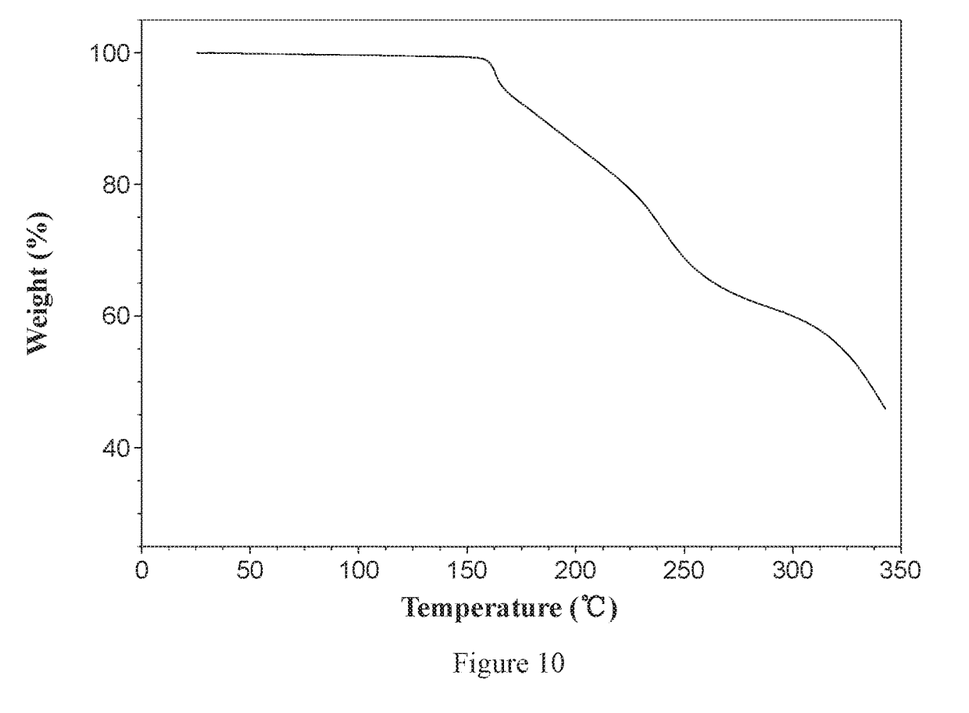
FIG. 10 is the TGA thermogram of Crystalline Form of Compound A of the present invention.

Its TGA thermogram is shown in FIG. 10, showing a weight loss of 0.3% before 100° C. It is anhydrous, with a decomposition temperature at 160° C.

Example 3

Acetone (3 mL) was added to entinostat (45 mg) to form a solution, slowly dripping in 1 mL of fumaric acid solution (0.8 molar equivalent, in acetone) to it. The mixture was stirred to crystallize for 1 day at 10° C., centrifuged, and dried under vacuum at room temperature to obtain Compound A (39 mg). Yield: 75%.

Example 4

Methanol (0.5 mL) and acetone (0.5 mL) were added to entinostat (100 mg), and was heated moderately to form a solution, then slowly dripping in 1 mL of fumaric acid solution (1 molar equivalent, in methanol) to it. The mixture was stirred to crystallize for 3 days at 40° C., centrifuged, and dried under vacuum at room temperature to obtain Compound A (75 mg). Yield: 65%.

Example 5

Compound A can also be obtained by replacing the solvents in Example 4 with the following solvents in the table below.

| Experiment Number | Solvent 1 | Solvent 2 |
|---|---|---|
| Experiment 1 | methanol | ethanol |
| Experiment 2 | ethanol | butanone |
| Experiment 3 | trifluoroethanol | acetone |
| Experiment 4 | isopropanol | acetone |
| Experiment 5 | n-propanol | acetone |
| Experiment 6 | sec-butanol | isopropanol |
| Experiment 7 | n-butanol | butanone |

Example 6

Ethanol (5 mL) was added to a mixture of entinostat (25 mg) and fumaric acid (3.9 mg) to form a solution. The solution was volatilized until solvent dryness at room temperature to obtain Compound A (26 mg). Yield: 90%.

Example 7

Ethanol (10 mL) was added to a mixture of entinostat (200 mg) and fumaric acid (37.0 mg), and was heated moderately to form a solution. The solution was volatilized until solvent dryness at room temperature to obtain Compound A (220 mg). Yield: 95%.

Example 8

Methanol (1 mL) was added to a mixture of entinostat (50 mg) and fumaric acid (15.4 mg) to form a solution. The solution was volatilized until solvent dryness at 40° C. to obtain Compound A (48 mg). Yield: 83%.

Example 9

Methanol (1.5 mL) and acetone (1.5 mL) were added to a mixture of entinostat (90 mg) and fumaric acid (25.0 mg) to form a solution. The solution was volatilized until solvent dryness at 10° C. to obtain Compound A (85 mg). Yield: 82%.

Example 10

The Compound A can also be obtained by replacing the solvents in Example 9 with the following solvents in the table below.

| Experiment Number | Solvent 1 | Solvent 2 |
|---|---|---|
| Experiment 1 | methanol | isopropanol |
| Experiment 2 | ethanol | trifluoroethanol |
| Experiment 3 | trifluoroethanol | butanone |
| Experiment 4 | isopropanol | acetone |
| Experiment 5 | n-propanol | acetone |
| Experiment 6 | sec-butanol | ethanol |
| Experiment 7 | n-butanol | acetone |

The samples prepared in Examples 3 to 10 had the same or similar XRPD patterns (not shown), DSC thermograms (not shown) and TGA thermograms (not shown) as the sample in Example 2. It indicates that the samples in Examples 3 to 10 and the sample in Example 2 are the same compounds.

Example 11

Ethanol (10 mL) was added to entinostat (100 mg) to form a solution, then slowly dripping in 2 mL of maleic acid solution (1 molar equivalent, in ethanol) to it. The mixture was stirred to crystallize for 2 days at room temperature, centrifuged, and dried under vacuum at room temperature to obtain Compound B (108 mg). Yield: 83%.

$^1$H-NMR (500 MHz, Methanol-d4) δ ppm: 8.65 (d, J=2.1 Hz, 1H), 8.56 (dd, J=5.2, 1.6 Hz, 1H), 8.03 (dt, J=7.9, 1.9 Hz, 1H), 7.98 (d, J=8.0 Hz, 2H), 7.58 (dd, J=7.9, 5.0 Hz, 1H), 7.45 (d, J=8.0 Hz, 2H), 7.32-7.24 (m, 1H), 7.20 (td, J=7.7, 1.5 Hz, 1H), 7.07 (dd, J=8.0, 1.4 Hz, 1H), 6.99 (td, J=7.6, 1.5 Hz, 1H), 6.30 (s, 2H), 5.23 (s, 2H), 4.40 (s, 2H), indicating that the molar ratio of entinostat to maleic acid in Compound B is 1:1.

Example 12

Ethanol (10 mL) was added to entinostat (300 mg) and was heated moderately to form a solution, then slowly dripping in 6 mL of maleic acid solution (1.2 molar equivalent, in ethanol) to it. The mixture was stirred to crystallize for 3 days at room temperature, centrifuged, and dried under vacuum at room temperature to obtain Compound B (349 mg). Yield: 89%.

Its XRPD pattern is shown in FIG. 5, showing that the compound is Crystalline Compound B.

Figure 9:
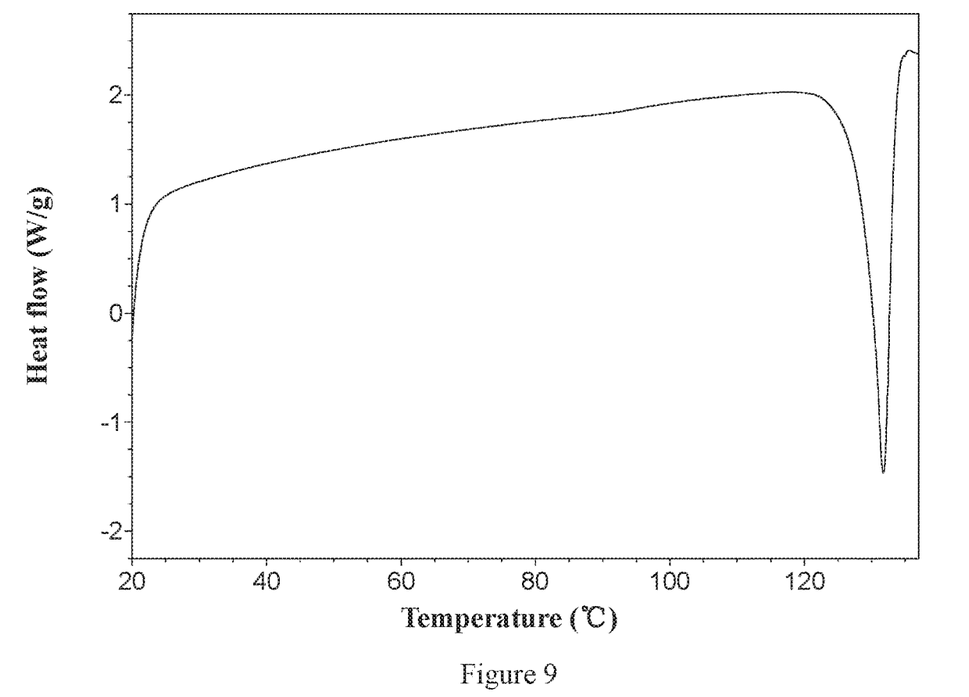
FIG. 9 is the DSC thermogram of Crystalline Form of Compound B of the present invention.

Its DSC thermogram is shown in FIG. 9, showing a melting point of 129° C.

Figure 11:
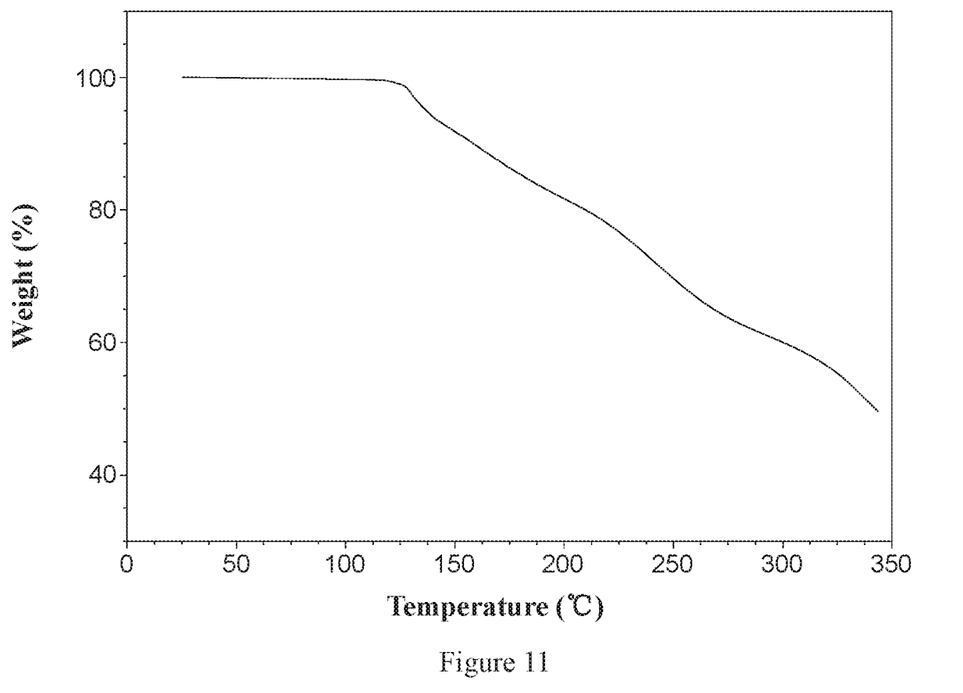
FIG. 11 is the TGA thermogram of Crystalline Form of Compound B of the present invention.
Figure 12:
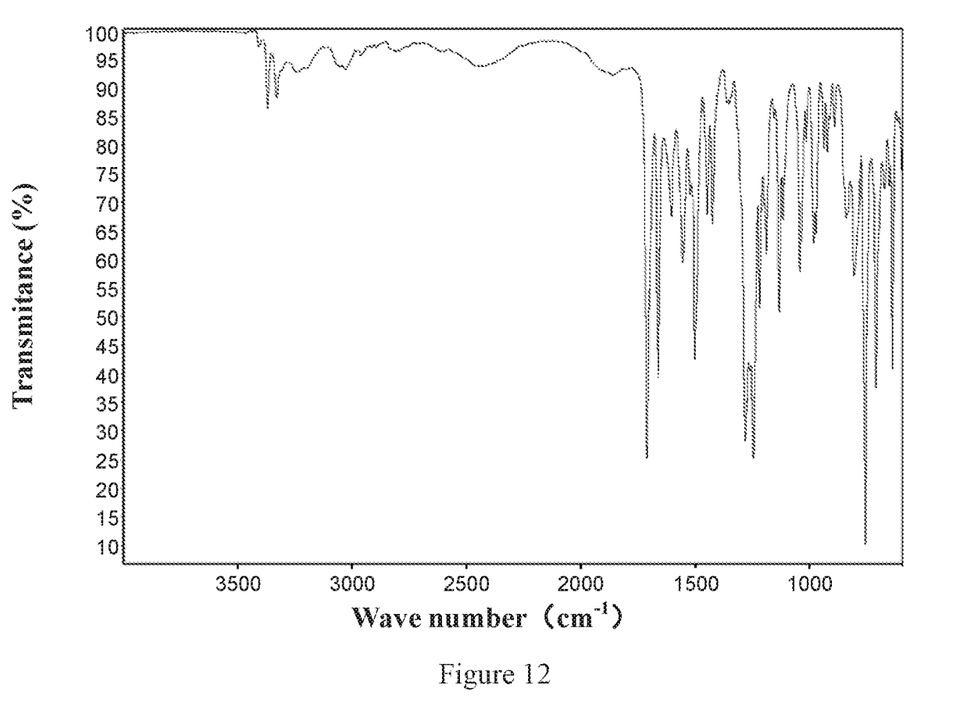
FIG. 12 is the IR pattern of Crystalline Form of Compound A of the present invention.
Figure 13:
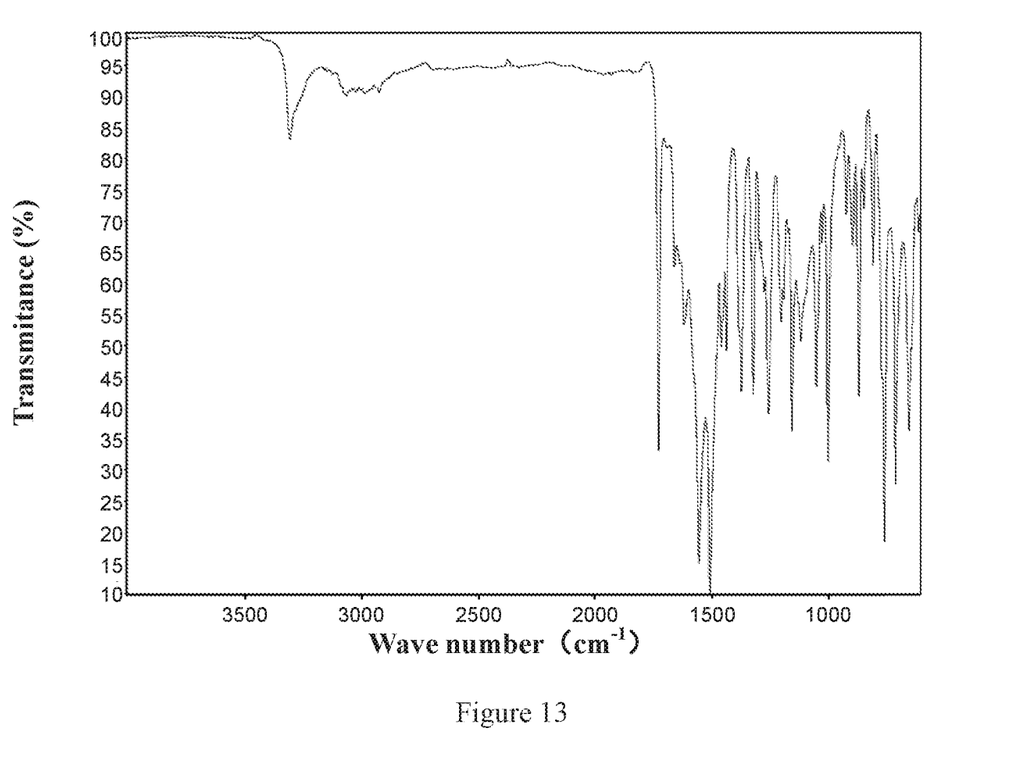
FIG. 13 is the IR pattern of Crystalline Form of Compound B of the present invention.

Its TGA thermogram is shown in FIG. 11, showing a weight loss of 0.3% before 100° C. It is anhydrous, with a decomposition temperature at 125° C.

Example 13

Butanone (1 mL) was added to entinostat (15 mg) to form a solution, then slowly dripping in 0.5 mL of maleic acid solution (1.3 molar equivalent, in acetone) to it. The mixture was stirred to crystallize for 1 day at 10° C., centrifuged, and dried under vacuum at room temperature to obtain Compound B (15 mg). Yield: 76%.

Example 14

Ethanol (0.5 mL) and acetone (0.5 mL) were added to entinostat (100 mg) and heated moderately to form a solution, then slowly dripping in 2 mL of maleic acid solution (1.5 molar equivalent, in ethanol) to it. The mixture was stirred to crystallize for 3 days at 40° C., centrifuged, and dried under vacuum at room temperature to obtain Compound B (99 mg). Yield: 76%.

Example 15

The Compound B can be obtained by replacing the solvents in Example 14 with the following solvents in the table below.

| Experiment Number | Solvent 1 | Solvent 2 |
|---|---|---|
| Experiment 1 | methanol | — |
| Experiment 2 | ethanol | butanone |
| Experiment 3 | trifluoroethanol | — |
| Experiment 4 | isopropanol | ethanol |
| Experiment 5 | n-propanol | butanone |
| Experiment 6 | sec-butanol | trifluoroethanol |
| Experiment 7 | n-butanol | butanone |

Example 16

Ethanol (40 mL) was added to a mixture of entinostat (200 mg) and maleic acid (61.7 mg) to form a solution. The solution was volatilized until solvent dryness at room temperature to obtain Compound B (245 mg). Yield: 94%.

Example 17

Ethanol (10 mL) was added to a mixture of entinostat (200 mg) and maleic acid (74.0 mg), and heated moderately to form a solution. The solution was volatilized until solvent dryness at room temperature to obtain Compound B (230 mg). Yield: 88%.

Example 18

Trifluoroethanol (2 mL) was added to a mixture of entinostat (100 mg) and maleic acid (46.3 mg), and it was heated moderately to form a solution. The solution was volatilized until solvent dryness at 10° C. to obtain Compound B (107 mg). Yield: 82%.

Example 19

Ethanol (1.5 mL) and acetone (1.5 mL) were added to a mixture of entinostat (120 mg) and maleic acid (55.5 mg), and it was heated moderately to form a solution. The solution was volatilized until solvent dryness at 40° C. to obtain Compound B (125 mg). Yield: 80%.

Example 20

The Compound B can be obtained by replacing the solvents in Example 19 with the following solvents in the table below.

| Experiment Number | Solvent 1 | Solvent 2 |
|---|---|---|
| Experiment 1 | methanol | — |
| Experiment 2 | ethanol | methanol |
| Experiment 3 | trifluoroethanol | acetone |
| Experiment 4 | acetone | — |
| Experiment 5 | n-propanol | isopropanol |
| Experiment 6 | sec-butanol | methanol |
| Experiment 7 | n-butanol | acetone |

The samples prepared in Examples 13 to 20 had the same or similar XRPD patterns (not shown), DSC thermograms (not shown) and TGA thermograms (not shown) as the sample in Example 12. It indicates that the samples in Examples 13 to 20 and the sample in Example 12 are the same compounds.

Example 21

Tetrahydrofuran (4 mL) was added to a mixture of entinostat (100 mg) and succinic acid (15.7 mg) to form a solution. The solution was volatilized until solvent dryness at room temperature to obtain Compound C (90 mg). Yield: 78%.

Its XRPD pattern shown in FIG. 6, indicates that the compound is Crystalline Compound C.

Example 22

Acetone (5 mL) was added to entinostat (80 mg) to form a solution, then slowly dripping in 1 mL of adipic acid solution (1.25 molar equivalent, in acetone) to it. The mixture was stirred to crystallize for 1 day at room temperature, centrifuged, and dried under vacuum at room temperature to obtain Compound D (86 mg). Yield: 77%.

Its XRPD pattern is shown in FIG. 7, showing that the compound is Crystalline Compound D.

Example 23

| Component | Dosage (mg) |
|---|---|
| Compound A (active ingredient basis) or Compound B (active ingredient basis) | 4 |
| starch | 407 |
| magnesium stearate | 3 |
| Total | 414 |

Compound A or Compound B, starch, and magnesium stearate were blended, sifted through 20 mesh sieve, and then filled into the hard capsule in an amount of 414 mg.

Example 24

| Component | Dosage (mg) |
| --- | --- |
| Compound A (active ingredient basis) or Compound B (active ingredient basis) | 8 |
| microcrystalline cellulose | 200 |
| silica colloid | 10 |
| magnesium stearate | 5 |
| Total | 223 |

The above components were blended and compressed into tablets, and each tablet weighed 223 mg.

Comparative Example 1

Entinostat, Compound A and Compound B in the present invention were tested for the apparent water solubility, and the operations were as follows:

Placed 3 mg of sample in a 100 mL Erlenmeyer flask in a water bath at 25° C.±2° C., added water by doubling, stirred at about 200 rpm/min, checked visually if the solution was clear. The interval between each addition of water was 3 minutes, and the maximum amount of water to add was 60 mL.

The results shown in the table below indicate that the water solubility of the Compound A and Compound B in the present invention is better than entinostat in the prior art.

| Compound | Solubility (mg/mL) |
| --- | --- |
| Compound A | 0.13 |
| Compound B | 1.01 |
| entinostat | <0.05 |

Comparative Example 2

Appropriate amounts of Crystalline Form of Compound A and Crystalline Form of Compound B in the present invention were used respectively for the phase stability test. The conditions were room temperature and high temperature (50° C.). The results are shown in the following table below:

| Conditions | Days | Crystal Form of Compound A | Crystal Form of Compound B |
| --- | --- | --- | --- |
| Room temperature | 7 | Crystalline form unchanged | Crystalline form unchanged |
| | 14 | Crystalline form unchanged | Crystalline form unchanged |
| High temperature | 7 | Crystalline form unchanged | Crystalline form unchanged |
| | 14 | Crystalline form unchanged | Crystalline form unchanged |

The results show that the phases of Crystalline Form of Compound A and Crystalline Form of Compound B in the present invention are unchanged after having been stored at room temperature and high temperature for 14 days, demonstrating good crystal stability.

Comparative Example 3

1. Appropriate amounts of entinostat and Compound A in the present invention were used respectively for HPLC analysis, the purity of the compounds and the maximum single impurity (RRT=1.403) were calculated.

2. Chemical stability tests of entinostat and Compound A in the present invention were performed. The conditions were as follows: room temperature, high temperature (40° C.), high humidity (75% RH), and acceleration (40° C.-75% RH), and the storage time is 14 days. Using HPLC analysis, the change of maximum single impurity (RRT=1.403), the change of the main ingredient level and the change of total impurities number were studied. The results are shown in the following table below:

| | | Entinostat | | | Compound A | | |
| --- | --- | --- | --- | --- | --- | --- | --- |
| Condition | Days | RRT = 1.403 (%) | Main ingredient (%) | Number of impurities (≥0.04%) | RRT = 1.403 (%) | Main ingredient (%) | Number of impurities (≥0.04%) |
| Room temperature | 0 | 1.42 | 98.4 | 4 | 0.12 | 99.9 | 0 |
| Room temperature | 14 | 1.42 | 98.4 | 4 | 0.13 | 99.9 | 0 |
| High temperature | 14 | 1.44 | 98.4 | 5 | 0.11 | 99.9 | 0 |
| High temperature | 14 | 1.43 | 98.4 | 5 | 0.11 | 99.9 | 0 |
| Speeded-up | 14 | 1.41 | 98.4 | 5 | 0.13 | 99.9 | 0 |

The results show that:

1. Compared with entinostat, Compound A of the present invention has significantly reduced level of maximum single impurity (RRT=1.403), and has fewer impurities and higher purity.

2. After having been stored for 14 days under the conditions of room temperature, high temperature, high humidity and acceleration, the impurity at RRT=1.403, the main ingredient and the number of impurities of both entinostat and Compound A of the present invention remained essentially unchanged.

The above results show that compared with entinostat, Compound A of the present invention has lower impurity level at RRT=1.403, less number of impurities, higher chemical purity and excellent chemical stability under the conditions of room temperature, high temperature, high humidity and acceleration, respectively.

Comparative Example 4

50 mg of entinostat from Preparation Example 1 and 50 mg of Compound B of the present invention were respectively stirred in 1.3 ml of methanol, heated to dissolve, after 1 hour, cooled to 4° C. for recrystallization, and were analyzed by HPLC. Experimental results: after recrystallization, the impurity level at RRT=1.403 in the entinostat sample was 1.42%, and the purity of the entinostat sample was 98.4%, both were the same as before recrystallization. The impurity level of RRT=1.403 in Compound B decreased from 1.53% before recrystallization to 1.27% after recrystallization, and its purity increased from 98.3% before recrystallization to 98.5% after recrystallization. The results show that Compound B of the present invention is easier to purify by recrystallization using organic solvents than the known entinostat.

The described above are only specific embodiments for illustrating the present invention, but without limiting it to that. Any changes or alternations, without creative work, made by those skilled in the art within the technical scope disclosed by the present invention, should fall within the scope of the present invention. Therefore, the scope of protection of the present invention shall be subject to the scope of protection defined in the claims.

What is claimed is:

1. A crystalline Compound A of formula (II):

wherein the X-ray powder diffraction pattern of the crystalline Compound A, expressed as 2θ angles, has the following characteristic peaks: 3.9°±0.2°, 13.4°±0.2°, 16.4°±0.2°, and 18.8°±0.2°.

2. The crystalline Compound A according to claim 1, wherein the X-ray powder diffraction pattern of the crystalline Compound A, expressed as 2θ angles, has the following characteristic peaks: 11.5°±0.2°, 15.3°±0.2°, 18.3°±0.2°, and 19.7°±0.2°.

3. The crystalline Compound A according to claim 2, wherein the X-ray powder diffraction pattern of the crystalline Compound A, expressed as 2θ angles, has the following characteristic peaks: 7.7°±0.2°, 10.9°±0.2°, 22.8°±0.2° and 26.2°±0.2°.

4. A method of preparing the crystalline Compound A according to claim 1, the method comprising:
(a) dissolving entinostat and fumaric acid respectively in a solvent to form a solution of entinostat and a solution of fumaric acid, then mixing the solution of entinostat and the solution of fumaric acid and stirring for crystallization, separating precipitated crystals, and drying to obtain the crystalline Compound A; wherein:
the solvent is an alcohol or a ketone;
the mass-volume ratio of entinostat to the solvent in the solution of entinostat ranges from 10 mg/mL to 100 mg/mL;
the molar ratio of entinostat to fumaric acid ranges from 1:0.5 to 1:1.0;
the duration for stirring is from 1 to 3 days; and
the operation is performed at 10° C. to 40° C.; or
(b) forming a solution of the mixture of entinostat and fumaric acid in a solvent, then drying the solvent by volatilization to obtain the crystalline Compound A; wherein:
the solvent is an alcohol or a ketone;
the mass-volume ratio of entinostat to the solvent ranges from 5 to 50 mg/mL;
the molar ratio of entinostat to fumaric acid ranges from 1:0.5 to 1:1.0; and
the volatilization is performed at 10° C. to 40° C.

5. The method according to claim 4, wherein the solvent is ethanol.

6. A pharmaceutical composition comprising a therapeutically effective amount of the crystalline Compound A according to claim 1, and at least one pharmaceutically acceptable carrier or additive.

7. A crystalline Compound B of formula (III):

wherein the X-ray powder diffraction pattern of the crystalline Compound B, expressed as 2θ angles, has the following characteristic peaks: 9.8°±0.2°, 15.9°±0.2°, 19.7°±0.2°, and 23 0.2°±0.2°.

8. The crystalline Compound B according to claim 7, wherein the X-ray powder diffraction pattern of the crystalline Compound B, expressed as 2θ angles, has the following characteristic peaks: 14.1°±0.2°, 14.8°±0.2°, 17.7°±0.2°, and 18.9°±0.2°.

9. The crystalline Compound B according to claim 8, wherein the X-ray powder diffraction pattern of the crystalline Compound B, expressed as 2θ angles, has the following characteristic peaks: 14.5°±0.2°, 21.4°±0.2°, 23.8°±0.2°, and 24.8°±0.2°.

10. A method of preparing the crystalline Compound B according to claim 7, the method comprising:
(a) dissolving entinostat and maleic acid respectively in a solvent to form a solution of entinostat and a solution of maleic acid, then mixing the solution of entinostat and the solution of maleic acid and stirring for crystallization, separating precipitated crystals, and drying to obtain the crystalline Compound B; wherein:
the solvent is an alcohol or a ketone;
the mass-volume ratio of entinostat to the solvent in the solution of entinostat ranges from 10 mg/mL to 100 mg/mL;

the molar ratio of entinostat to maleic acid ranges from 1:1.0 to 1:1.5;
the duration for stirring is from 1 to 3 days; and
the operation is performed at room temperature; or
(b) forming a solution of the mixture of entinostat and maleic acid in a solvent, then drying the solvent by volatilization to obtain the crystalline Compound B; wherein:
the solvent is an alcohol or a ketone;
the mass-volume ratio of entinostat to the solvent ranges from 5 to 50 mg/mL;
the molar ratio of entinostat to maleic acid ranges from 1:1.0 to 1:1.5; and
the volatilization is performed at room temperature.

11. The method according to claim 10, wherein the solvent is ethanol.

12. A pharmaceutical composition comprising a therapeutically effective amount of the crystalline Compound B according to claim 7, and at least one pharmaceutically acceptable carrier or additive.

\* \* \* \* \*

UNITED STATES PATENT AND TRADEMARK OFFICE
CERTIFICATE OF CORRECTION

PATENT NO. : 11,208,382 B2
APPLICATION NO. : 16/634797
DATED : December 28, 2021
INVENTOR(S) : Sheng et al.

It is certified that error appears in the above-identified patent and that said Letters Patent is hereby corrected as shown below:

On the Title Page

Item (86), in "§ 371 (c)(1),(2) Date:", Line 1, delete "Apr. 17, 2020" and insert -- Jan. 28, 2020 --, therefor.

Signed and Sealed this
Tenth Day of May, 2022

Katherine Kelly Vidal
*Director of the United States Patent and Trademark Office*